(12) United States Patent
Nakamura et al.

(10) Patent No.: US 8,910,537 B2
(45) Date of Patent: Dec. 16, 2014

(54) HOLDING ARM APPARATUS FOR MEDICAL TOOL

(75) Inventors: Katsushige Nakamura, Tokyo (JP); Masao Doi, Tokyo (JP); Tatsuya Hashimoto, Tokyo (JP); Masakazu Nakamura, Tokyo (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 901 days.

(21) Appl. No.: 12/997,285

(22) PCT Filed: May 20, 2009

(86) PCT No.: PCT/JP2009/059244
§ 371 (c)(1),
(2), (4) Date: Dec. 10, 2010

(87) PCT Pub. No.: WO2009/150925
PCT Pub. Date: Dec. 17, 2009

(65) Prior Publication Data
US 2011/0162476 A1 Jul. 7, 2011

(30) Foreign Application Priority Data

Jun. 12, 2008 (JP) ................. 2008-154479

(51) Int. Cl.
*B25J 18/04* (2006.01)
*A61B 19/00* (2006.01)

(52) U.S. Cl.
CPC ........... *A61B 19/26* (2013.01); *A61B 2019/263* (2013.01); *A61B 2019/266* (2013.01); *Y10S 901/21* (2013.01)
USPC ........................................ 74/490.04; 901/21

(58) Field of Classification Search
USPC .............................. 74/490.04, 490.01; 901/21
See application file for complete search history.

(56) References Cited

U.S. PATENT DOCUMENTS 6,688,189 B2 * 2/2004 Hashimoto et al. ........ 74/490.04
7,416,163 B2 8/2008 Gaida et al.
(Continued)

FOREIGN PATENT DOCUMENTS

CA 2167889 10/1996
DE 10142564 A1 4/2002
(Continued)

OTHER PUBLICATIONS

International Preliminary Report on Patentability and Written Opinion, PCT/JP2009/059244 (6 pages).

(Continued)

*Primary Examiner* — Troy Chambers
*Assistant Examiner* — Terence Boes
(74) *Attorney, Agent, or Firm* — Edell, Shapiro & Finnan, LLC

(57) ABSTRACT

A holding arm apparatus 1 is configured to connect upper and lower timing pulleys 5A and 6A of a vertical arm unit 4 to each other with a timing belt 15, to widen the range of rotation angle of a horizontal arm unit 5 and allow the position and angle of an endoscope 20 held at a front end of the horizontal arm unit 5 to be widely changed. The horizontal arm unit 5 and a counterweight 6 turn by the same angle, to maintain a weight balance by the counterweight 6. Using the timing belt 15 reduces the total weight and operation noise of the holding arm apparatus 1. Accordingly, the apparatus is appropriate for a medical front.

4 Claims, 12 Drawing Sheets

(56) References Cited

U.S. PATENT DOCUMENTS

| | | |
|---|---|---|
| 7,665,702 B2 | 2/2010 | Gaida et al. |
| 2003/0159535 A1* | 8/2003 | Grover et al. ............. 74/490.04 |
| 2011/0167946 A1* | 7/2011 | Kim et al. .................. 74/490.04 |

FOREIGN PATENT DOCUMENTS

| | | |
|---|---|---|
| EP | 1915965 A2 | 4/2008 |
| JP | 716239 | 1/1995 |
| JP | 2001300871 | 10/2001 |
| JP | 2002165804 | 6/2002 |
| JP | 2004154174 | 6/2004 |
| JP | 2005211667 | 8/2005 |
| JP | 2006102155 | 4/2006 |
| JP | 200886711 | 4/2008 |

OTHER PUBLICATIONS

German Patent Office, Office Action 11 2009 001 412.7, Aug. 10, 2011 with English Translation 15 pages.

* cited by examiner

HOLDING ARM APPARATUS FOR MEDICAL TOOL

TECHNICAL FIELD

The present invention relates to a holding arm apparatus for medical tool.

BACKGROUND TECHNOLOGY

In a medical field, various tools are used in recent years. For example, endoscopes, ultrasonic echo probes, brain retractors, aspiration tubes, and other kinds of tools are used. Such a medical tool must be held for a patient at a proper position. For this, a holding arm apparatus using a parallel linkage is employed.

The holding arm apparatus of this type holds a medical tool at an end of an arm of the parallel linkage (including a belt driving mechanism) and has a counterweight at the other end of the arm. For example, Japanese Unexamined Patent Application Publications No. 2002-165804 and No. 2005-211667 disclose apparatuses capable of maintaining a weight balance with respect to a medical tool, setting the medical tool at a required position and angle, and fixing the state with clutches.

SUMMARY OF INVENTION

The arm of the related art, however, achieves a small rotation angle because the parallel linkage that supports the arm is unable to widely change the position or angle of the medical tool.

In consideration of the related art, the present invention provides a medical tool holding arm apparatus, capable of widely changing the position and angle of a medical tool.

Means to Solve the Problems

According to a technical aspect of the present invention, the medical tool holding arm apparatus includes a base unit set on a floor, a support unit uprightly arranged on the base unit, a vertical arm unit whose middle part is rotatably supported with a rotary shaft at an upper end of the support unit, a horizontal arm unit whose base is rotatably supported with a rotary shaft at an upper end of the vertical arm unit and whose front end supports a medical tool, a counterweight supported with a rotary shaft at a lower end of the vertical arm unit, and a clutch to put an optional one of the rotary shafts into a rotational state or a fixed state. The rotary shaft at the upper end of the vertical arm unit is integral with the horizontal arm unit, the rotary shaft at the lower end thereof is integral with the counterweight, and a loop-like torque transmission member is stretched between the upper and lower rotary shafts.

MODE OF IMPLEMENTING INVENTION

Figure 1:
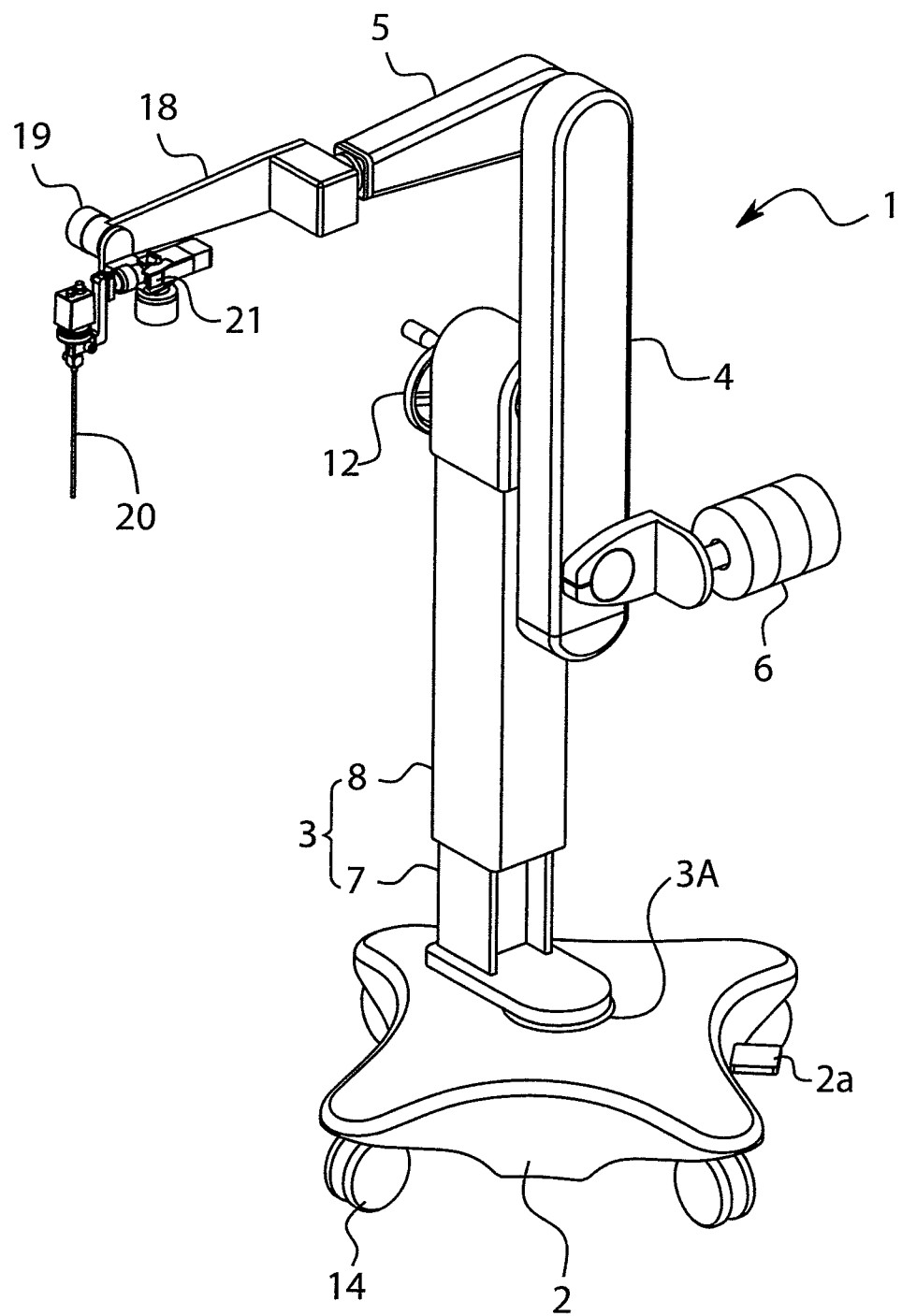
FIG. 1 is a perspective view illustrating a holding arm apparatus according to an embodiment of the present invention.
Figure 2:
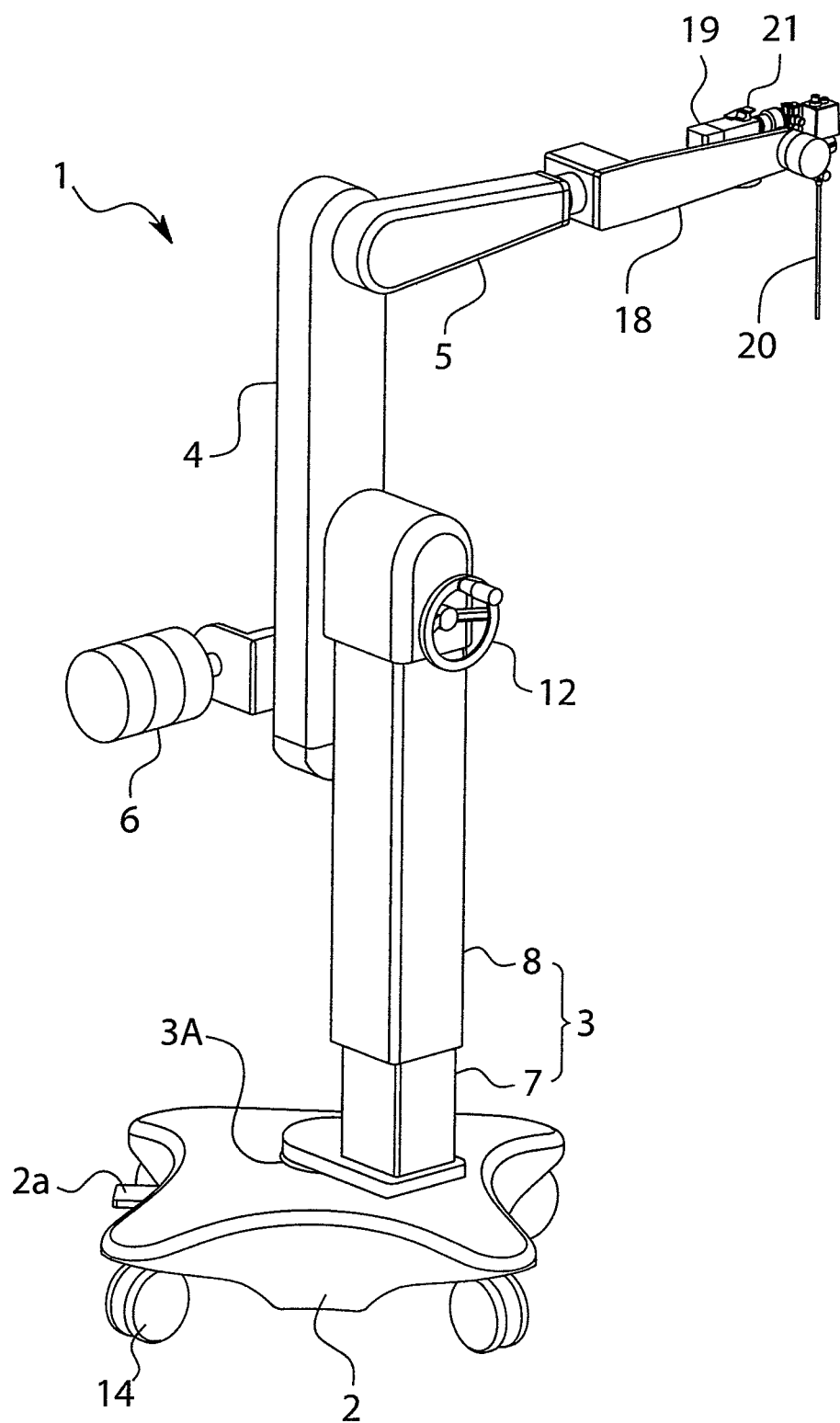
FIG. 2 is a perspective view illustrating the holding arm apparatus seen from another angle.

A preferred embodiment of the present invention will be explained with reference to the drawings. A holding arm apparatus 1 according to the present embodiment includes a base unit 2, a support unit 3, a vertical arm unit 4, a horizontal arm unit 5, and a counterweight 6.

The base unit 2 has casters 14 at four corners to move along a floor and a foot-type brake mechanism 2a to fix the casters 14 in a position to the floor.

The support unit 3 is upright at a position shifted from a rotary shaft 3A that is at the center of the base unit 2. The support unit 3 is horizontally rotatable around the rotary shaft 3A. The rotary shaft 3A has a clutch (not illustrated) to immobilize the rotary shaft 3A. The clutch according to the embodiment is an air-type clutch driven by compressed air. It may be an electromagnetic clutch.

The support unit 3 has a stationary support 7 rotatably fixed to the base unit 2 and a movable support 8 vertically slidable along the stationary support 7.

Figure 8:
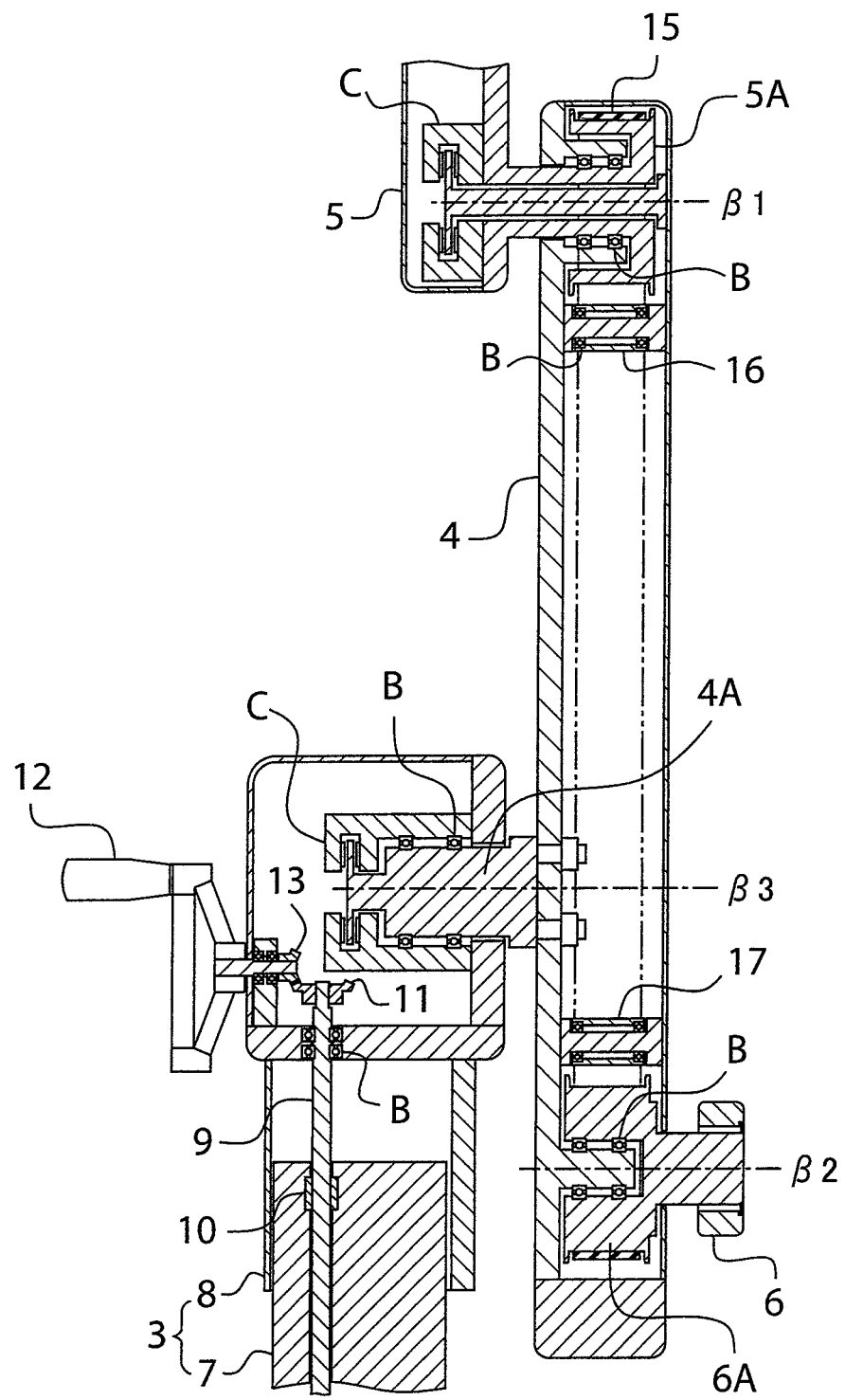
FIG. 8 is a sectional view illustrating the inside of a vertical arm unit and support unit.

As illustrated in FIG. 8, a threaded bar 9 extends from an upper end of the movable support 8 to the stationary support 7. The threaded bar 9 is rotatable with a bearing B and engages with a nut 10 arranged on the stationary support 7.

An upper end of the threaded bar 9 is provided with a bevel gear 11. The bevel gear 11 engages with another bevel gear 13 arranged on a rotary shaft of a handle 12. Torque applied on the handle 13 is transmitted through the bevel gears 11 and 13 to the threaded bar 9. When the threaded bar 9 turns, the movable support 8 vertically moves along the stationary support 7.

An upper end of the support unit 3 is provided with a rotary shaft 4A that is in a horizontal direction and is rotatable with a bearing B. The rotary shaft 4A is integrally fixed to a lower middle position of the vertical arm unit 4. Accordingly, the vertical arm unit 4 is rotatable around the rotary shaft 4A relative to the support unit 3.

The rotary shaft 4A is provided with a clutch C that frees and locks the rotation of the rotary shaft 4A by virtue of pressure of compressed air.

At upper and lower parts of the vertical arm unit 4, rotatably arranged with bearings B are timing pulleys 5A and 6A serving as rotary shafts. Namely, the vertical arm unit 4 has the rotary shaft with a theoretical axis β1 fixed in position to the upper end (first end) thereof and the rotary shaft with a theoretical axis β2 fixed in position to the lower end (second end) thereof.

The timing pulley 5A at the upper end is integral with a base end of the horizontal arm unit 5 and turns in the same direction as the horizontal arm unit 5. The upper timing pulley 5A is freely rotated and locked with a clutch C arranged in the horizontal arm 5. The timing pulley 6A at the lower end is integral with the counterweight 6 and turns in the same direction as the counterweight 6. The horizontal arm unit 5 and counterweight 6 extend in opposite directions and are in parallel with each other. The counterweight 6 generates torque about the rotation axis β2.

The upper and lower timing pulleys 5A and 6A each have recesses, and around the timing pulleys 5A and 6A, a timing belt 15 serving as a torque transmission member is stretched. The upper and lower timing pulleys 5A and 6A and timing belt form a torque transmission mechanism equivalent to a parallel linkage composed of vertical link elements (β1-β2) fixed relative to the vertical arm unit 4 and horizontal links that are radiuses of the timing pulleys 5A and 6A. The vertical arm unit 4 has a link casing, is made of a rigid material, and has a hollow structure to accommodate the timing pulleys 5A and 6A and timing belt 15.

Recesses of the timing belt 15 engage with the recesses of the timing pulleys 5A and 6A, to correctly transmit rotation and torque between them. As a result, without regard to attitudes of the horizontal arm unit 5 and vertical arm unit 4, torque of the horizontal arm unit 5 and an endoscope 20 about the rotation axis β1 is always compensated by torque of the counterweight 6 about the rotation axis β2.

Figure 9:
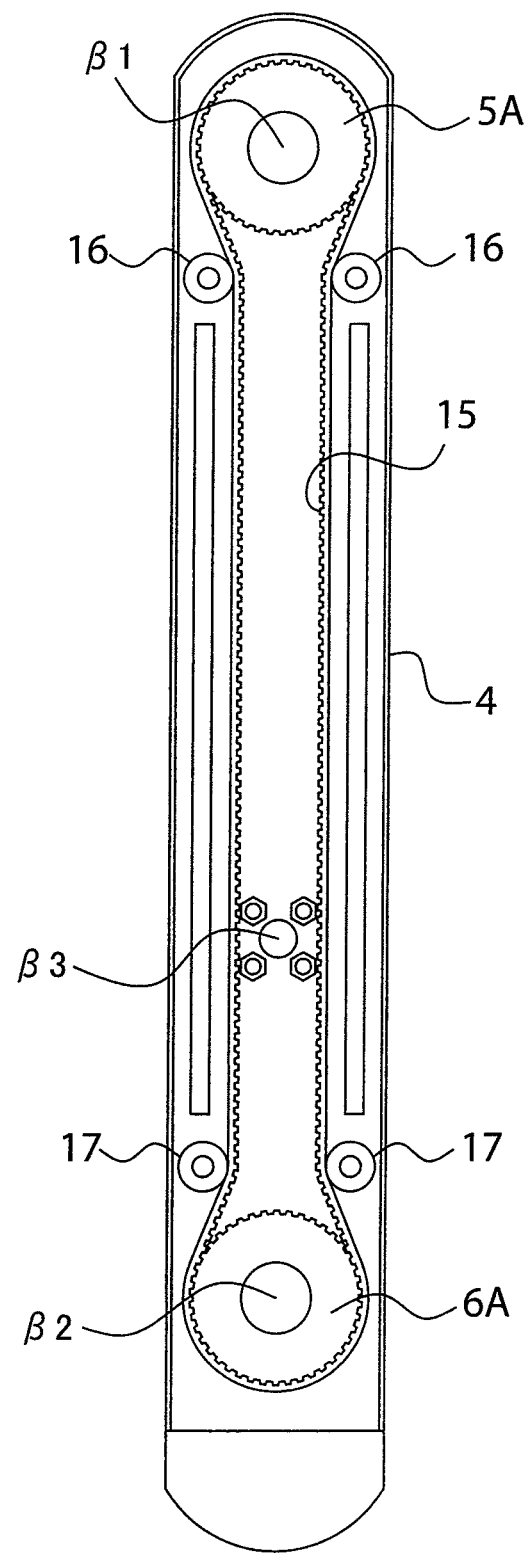
FIG. 9 is a side view illustrating the inside of the vertical arm unit.

At proximal positions of the upper and lower timing pulleys 5A and 6A, there are tension rollers 16 and 17. The tension rollers 16 and 17 are freely rotatable with bearings B, and in addition to tension provided by the vertical links (β1-β2) fixed to the vertical arm unit 5, produce tension by narrowing distances between facing parts of the timing belt 15. Narrowing the distances of the timing belt 15 increases contact areas between the timing belt 15 and the timing pulleys 5A and 6A as illustrated in FIG. 9, to improve a torque transmission capability of the timing belt 15.

A front arm 18 of the horizontal arm unit 5 is freely rotatable around an axial line of the horizontal arm unit 5 and is switched between a free state and a locked state with a clutch (not illustrated). An end of the front arm 18 is provided with an attachment 19 to hold a medical tool, i.e., the endoscope 20.

The attachment 19 has a switch lever 21. An operator grasps the attachment 19 with his or her hand and pushes the switch lever 21. Then, compressed air is supplied to free all clutches C. If the operator releases the hand from the switch lever 21, all clutches C are locked. Accordingly, the operator holds the attachment 19 with his or her hand and pushes the switch lever 21 to entirely free the holding arm apparatus 1, moves the endoscope 20 to a required position as well as inclination, and releases the hand from the switch lever 21, to automatically fix the position.

According to the present embodiment, the handle 12 is used to adjust the height of the support unit 3 and optimize the position of the horizontal arm unit 5 according to the height of a patient.

Figure 3:
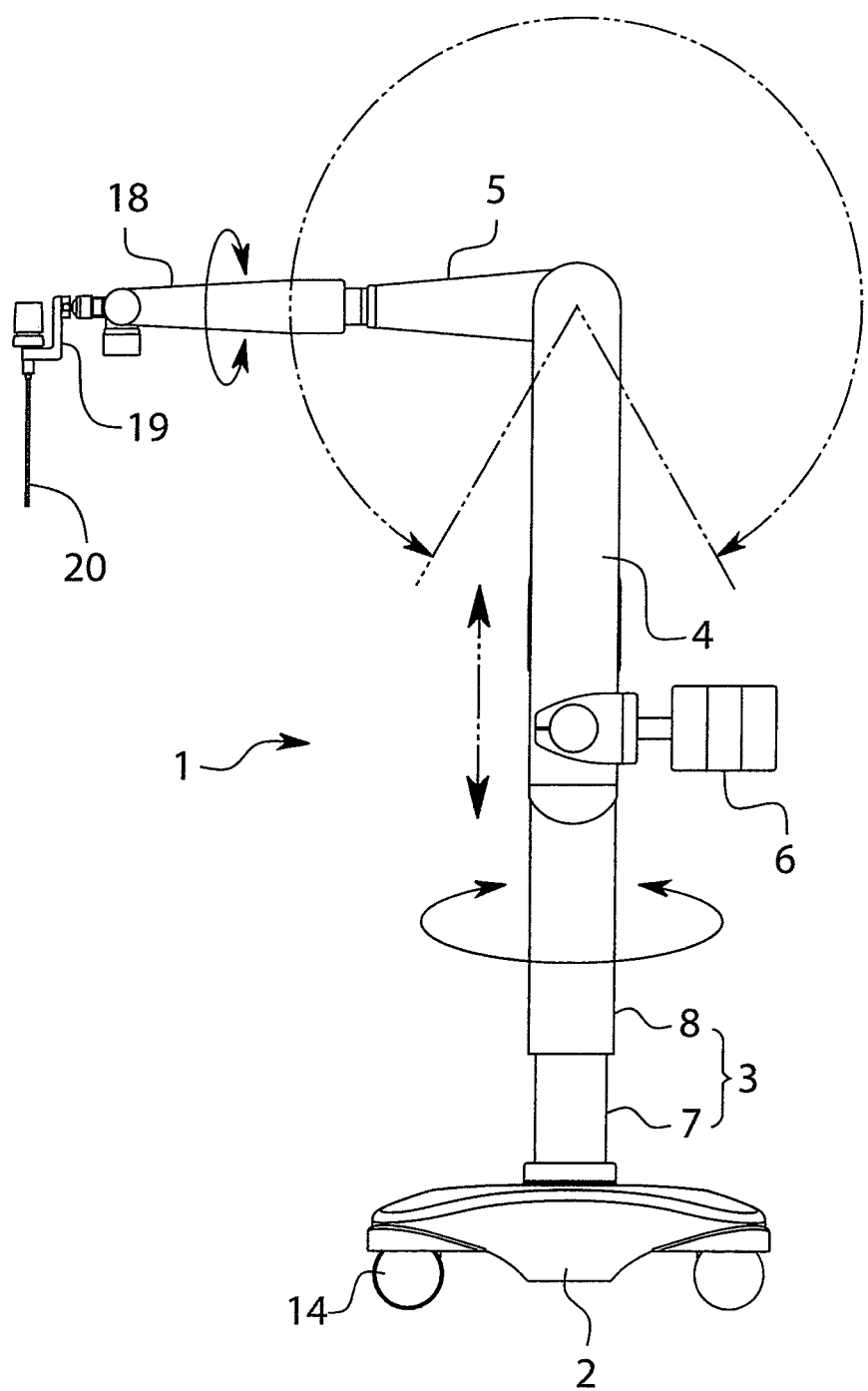
FIG. 3 is a side view illustrating the holding arm apparatus.
Figure 4:
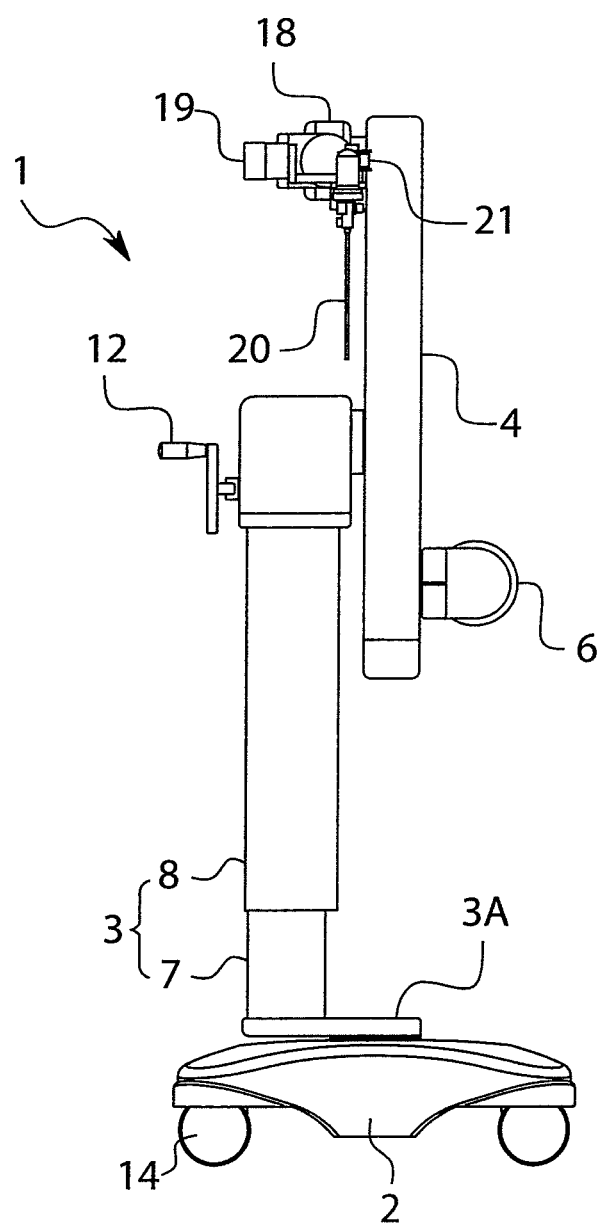
FIG. 4 is a front view illustrating the holding arm apparatus.
Figure 5:
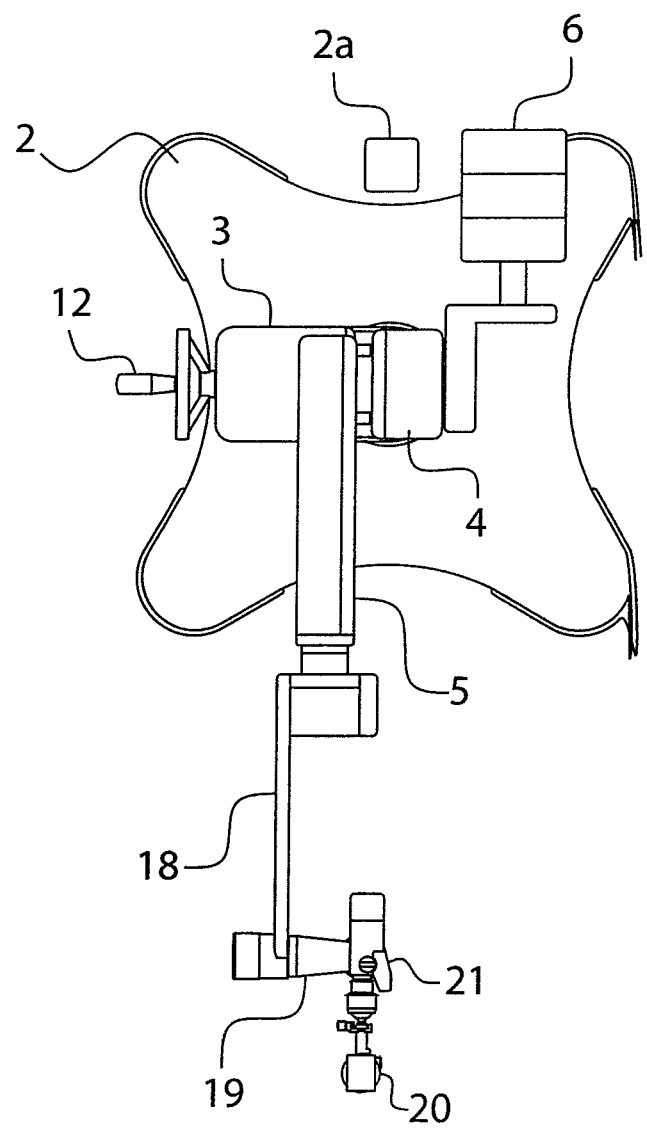
FIG. 5 is a plan view illustrating the holding arm apparatus.

The horizontal arm unit 5 and counterweight 6 turn together with the timing belt 15. As illustrated in FIG. 3, the counterweight 6 keeps a weight balance of the horizontal arm unit 5, and in this state, the horizontal arm unit 5 is freely turned around the rotation axis β1 even over 180 degrees. In practice, it can be turned within a range that does not interfere with the support unit 3.

Figure 6:
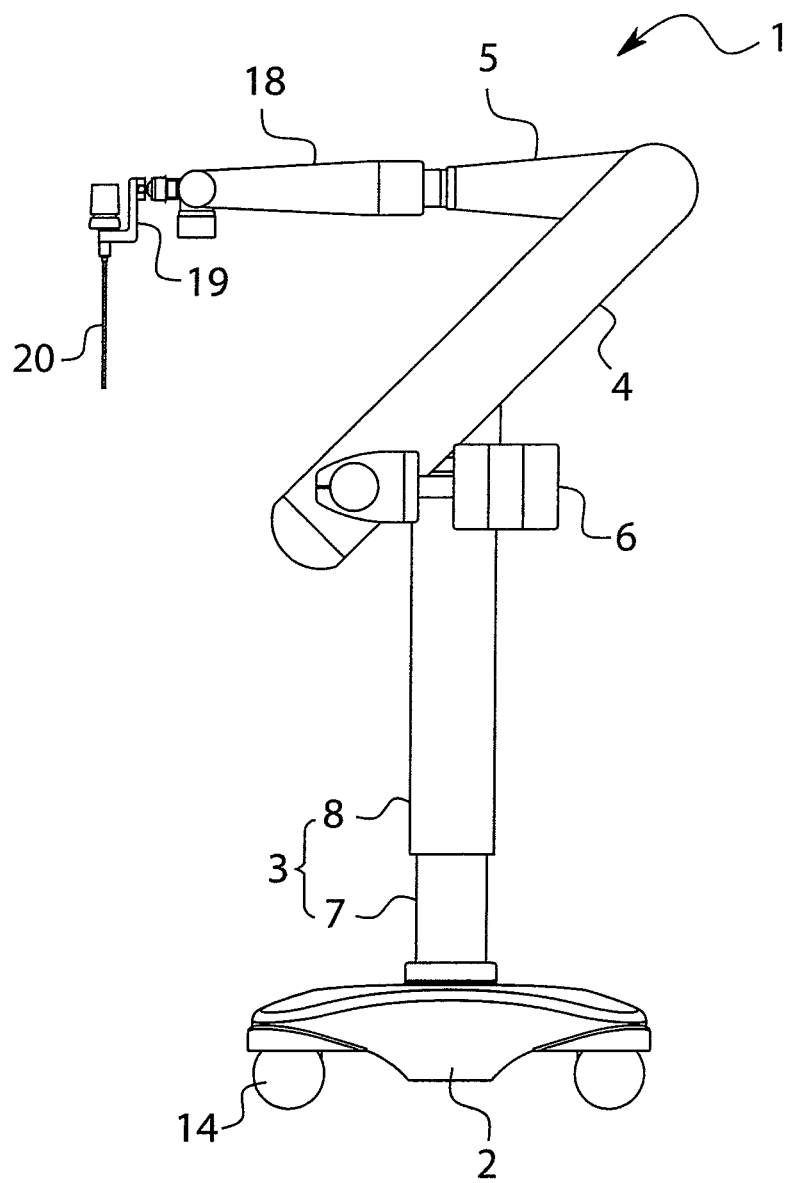
FIG. 6 is a side view illustrating an usage example of the holding arm apparatus.
Figure 7:
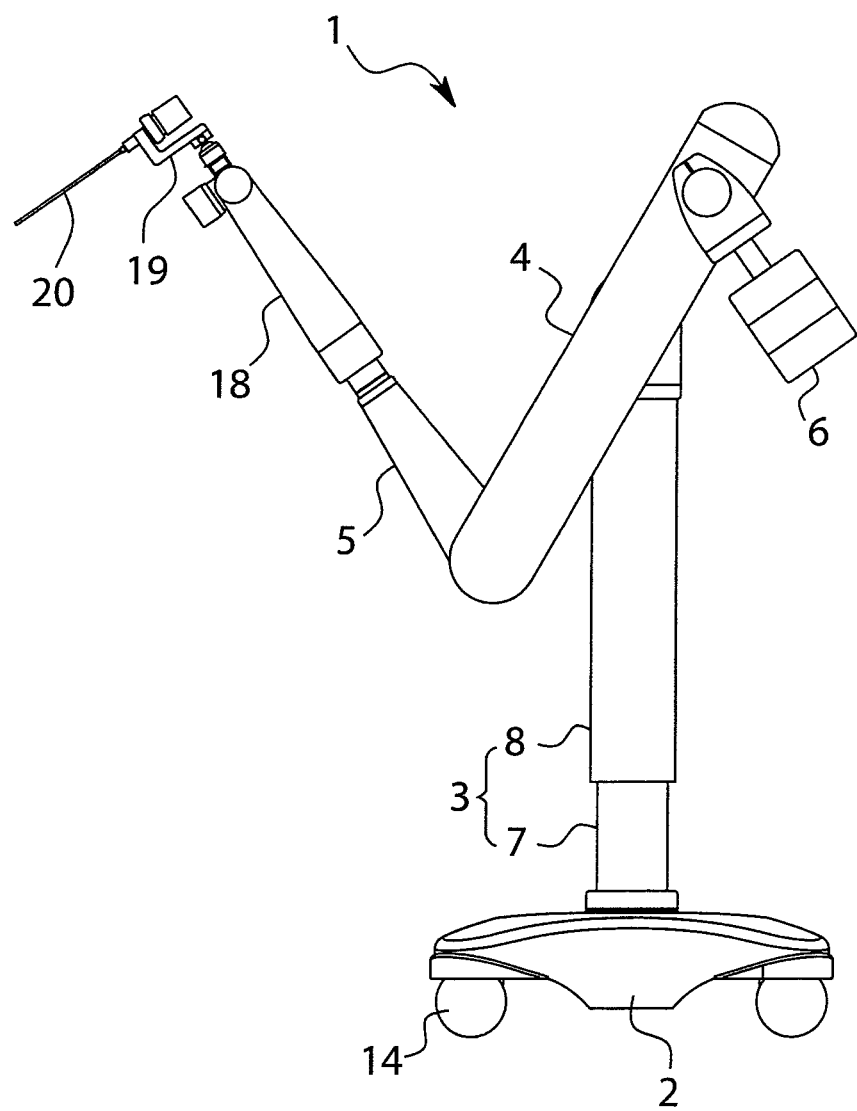
FIG. 7 is a side view illustrating another usage example of the holding arm apparatus.

As illustrated in FIGS. 6 and 7, the vertical arm unit 4 can freely be turned around a rotation axis β3 even over 180 degrees, so that a combination of the degrees of freedom of the vertical arm unit 4 and horizontal arm unit 5 allows the endoscope 20 to be moved in a wide range.

Figure 10:
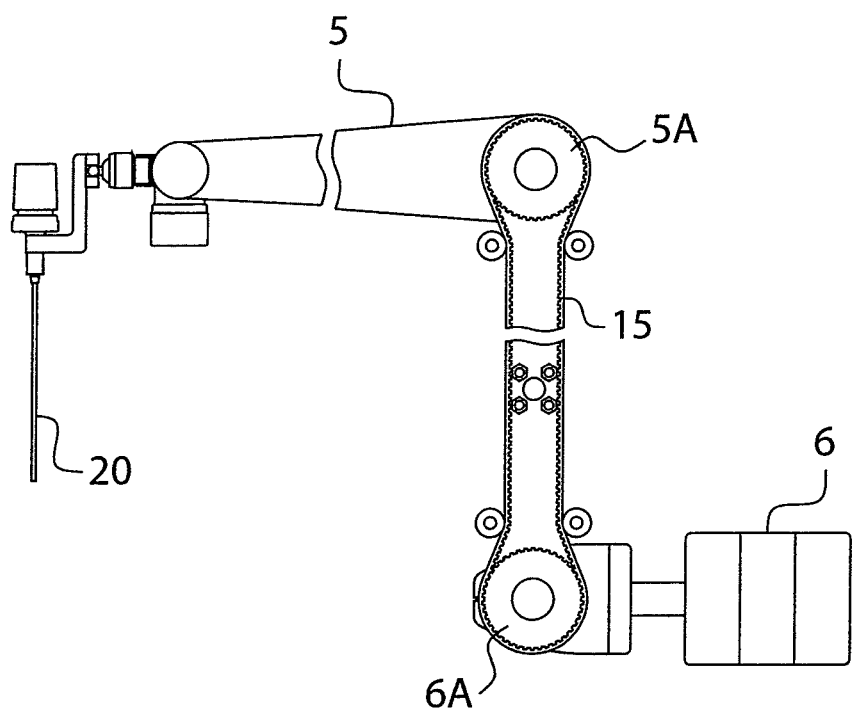
FIG. 10 is a side view illustrating a state of a horizontal arm unit oriented in a certain direction.
Figure 11:
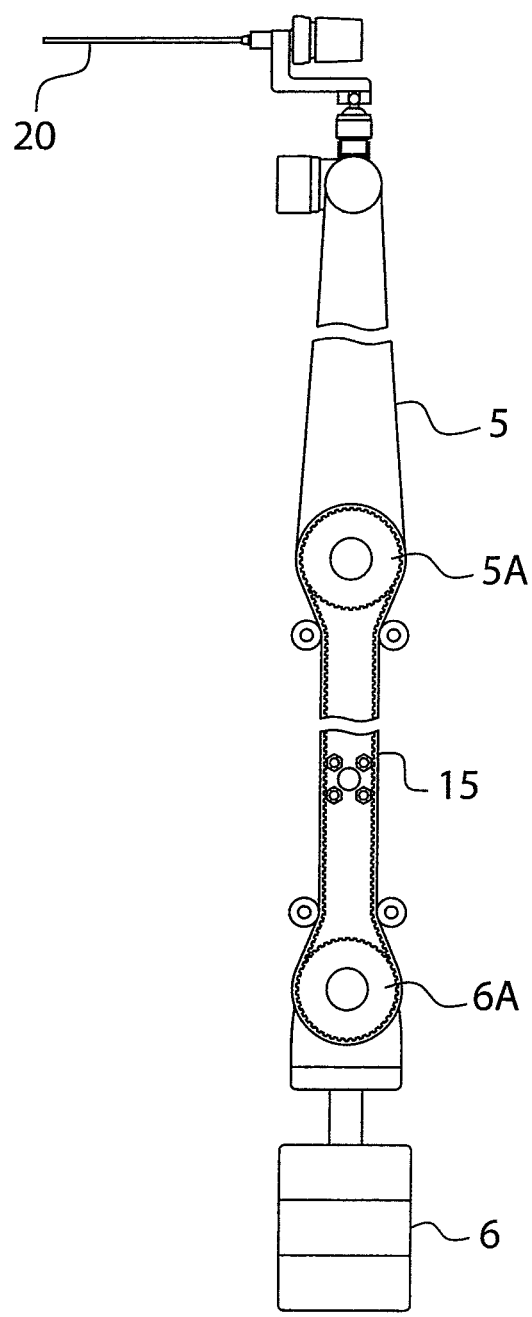
FIG. 11 is a side view illustrating a state of the horizontal arm unit oriented upward.
Figure 12:
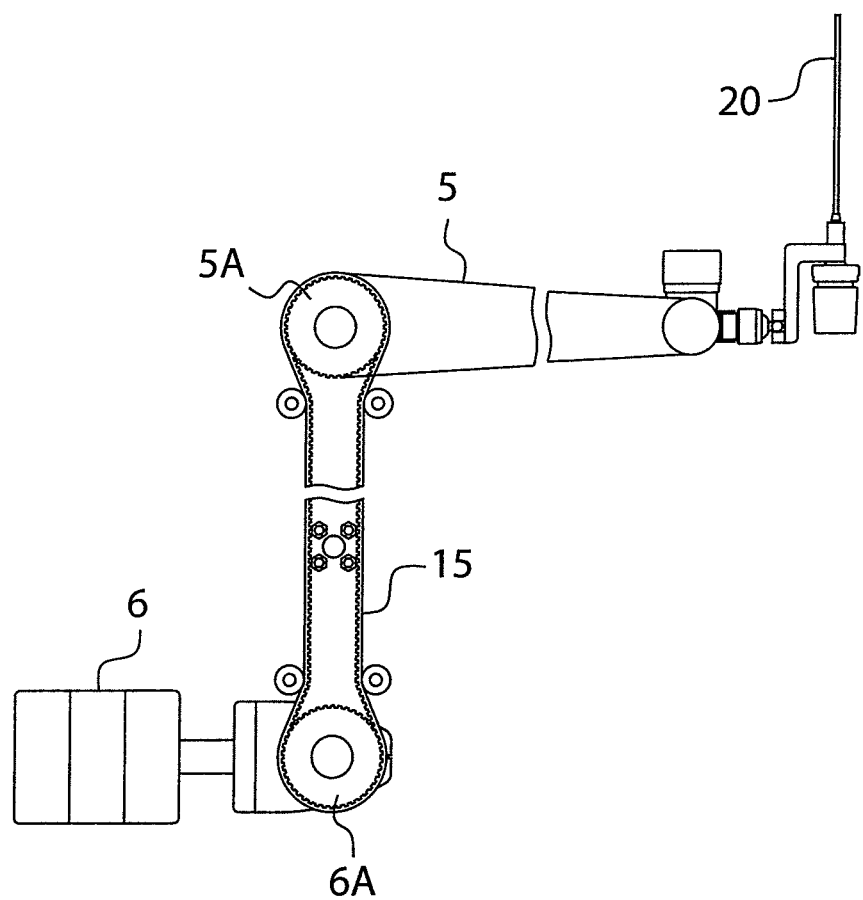
FIG. 12 is a side view illustrating a state of the horizontal arm oriented in an opposite direction.

Namely, as illustrated in FIGS. 10 to 12, the horizontal arm unit 5 oriented in a certain direction (FIG. 10) can be turned to a straight upright position (FIG. 11) and to an oppositely oriented position (FIG. 12). In each of the positions of FIGS. 10 and 12, the horizontal arm unit 5 can further be lowered if not interfering with the support unit 3, thereby expanding the moving range of the horizontal arm unit 5.

In this way, the range of rotation angle of the horizontal arm unit 5 is expanded to allow the position and angle of the endoscope 20 held at the front end of the horizontal arm unit 5 to be widely changed. This improves the operability of the holding arm apparatus 1.

For example, as illustrated in FIG. 6, the vertical arm unit 4 is retracted toward the support unit 3 and the horizontal arm unit 5 is lowered, to bring the endoscope 20 closer to the support unit 3. As illustrated in FIG. 7, the vertical arm unit 4 is oriented downward and the horizontal arm unit 5 is lifted, to face the endoscope 20 to a patient from below.

According to the present embodiment, the timing belt 15 that is light is used as the torque transmission member. This reduces the total weight of the holding arm apparatus 1. In addition, the timing belt 15 causes smaller operation noise compared with other gear transmission mechanisms, and therefore, is appropriate for a medical front that must be quiet.

The torque transmission member may be, instead of the timing belt 15, a timing chain or any other member.

Effect of Invention

According to the technical aspect of the present invention, the upper and lower rotary shafts of the vertical arm unit are connected to each other through the torque transmission member. This widens the range of rotation angle of the horizontal arm unit, to allow the position of a medical tool held at a front end of the horizontal arm unit to be widely changed. The horizontal arm unit and counterweight turn by the same angle, to secure a weight balance by the counterweight.

The timing belt is used as the torque transmission member, to reduce the total weight and operation noise of the apparatus. Accordingly, the apparatus is appropriate for a medical front.

The vertical arm unit is provided with the tension rollers to narrow distances between facing parts of the timing belt. This increases contact areas of the rotary shafts and improves a torque transmission capability.

The torque transmission member is not directly touchable from the outside, to improve safety.

(United States Designation)

In connection with United States designation, this international patent application claims the benefit of priority under 35 U.S.C. 119(a) to Japanese Patent Application No. 2008-154479 filed on Jun. 12, 2008 whose disclosed contents are cited herein.

The invention claimed is:

1. A medical tool holding arm apparatus, comprising:
a base unit set on a floor;
a support unit uprightly arranged on the base unit, the support unit comprising a stationary support that is rotatably fixed to the base unit and a movable support that is vertically slidable along the stationary support;
a vertical arm unit having an intermediate part that is rotatably supported with a third rotary shaft that is fixed in position at an upper end of the movable support of the support unit, and configured to be able to turn about the third rotary shaft over 180 degrees;
a horizontal arm unit having a base that is rotatably supported with a first rotary shaft having a rotation center that is fixed in position at a first end of the vertical arm unit, a front end of the horizontal arm unit supporting a medical tool, and configured to be able to turn about the first rotary shaft over 180 degrees;

a counterweight rotatably supported with a second rotary shaft having a rotation center that is fixed in position at a second end of the vertical arm unit;

a clutch configured to put at least one of the first, second, and third rotary shafts into a freely rotatable state or a fixed state; and a torque transmission mechanism having a torque transmission member stretched between the first and second rotary shafts and configured to transmit torque of the counterweight about the second rotary shaft and torque of the horizontal arm unit about the first rotary shaft to each other.

2. The medical tool holding arm apparatus according to claim 1, wherein the torque transmission member is a timing belt.

3. The medical tool holding arm apparatus according to claim 2, comprising a pair of tension rollers configured to narrow a distance between parts of the timing belt that face each other in the vertical arm unit and thereby strengthen tension.

4. The medical tool holding arm apparatus according to claim 1, wherein the vertical arm unit is a link casing having a hollow structure to accommodate the torque transmission member.

* * * * *